United States Patent [19]

Yan

[11] Patent Number: 4,804,801

[45] Date of Patent: Feb. 14, 1989

[54] PROCESS FOR CONVERTING $C_2$ TO $C_8$ ALIPHATICS TO AROMATICS OVER A METAL-ACTIVATED ZEOLITE

[75] Inventor: Tsoung Y. Yan, Philadelphia, Pa.

[73] Assignee: Mobil Oil Corporation, New York, N.Y.

[21] Appl. No.: 205,564

[22] Filed: Jun. 7, 1988

Related U.S. Application Data

[63] Continuation of Ser. No. 905,101, Sep. 8, 1986, abandoned.

[51] Int. Cl.$^4$ ............................................ C07C 15/393
[52] U.S. Cl. ................................. 585/407; 585/415; 585/417; 585/418
[58] Field of Search ................ 585/407, 415, 417, 418

[56] References Cited

U.S. PATENT DOCUMENTS

| | | | |
|---|---|---|---|
| 3,890,218 | 6/1975 | Morrison | 208/135 |
| 4,097,367 | 6/1978 | Haag et al. | 208/135 |
| 4,120,910 | 10/1978 | Chu | 260/673 |
| 4,157,293 | 6/1979 | Plank et al. | 208/135 |
| 4,197,214 | 4/1980 | Chen et al. | 585/407 |
| 4,350,835 | 9/1982 | Chester et al. | 585/415 |
| 4,392,989 | 7/1983 | Chu et al. | 585/415 |
| 4,465,884 | 8/1984 | Degnan et al. | 585/415 |
| 4,490,569 | 12/1984 | Chu et al. | 585/415 |

FOREIGN PATENT DOCUMENTS

| | | |
|---|---|---|
| 0040444 | 11/1981 | European Pat. Off. . |
| 0021475 | 9/1983 | European Pat. Off. . |
| 0036683 | 3/1984 | European Pat. Off. . |

*Primary Examiner*—Curtis R. Davis
*Attorney, Agent, or Firm*—Alexander J. McKillop; Michael G. Gilman; Malcolm D. Keen

[57] ABSTRACT

A catalytic process is provided for converting feedstock containing $C_2$ to $C_8$ aliphatic hydrocarbons to aromatics by contacting said feedstocks, under conversion conditions, with a balanced acid/hydrogenation dual function catalyst comprising as the acid component a crystalline zeolite catalyst having a Constraint Index of about 1 to 12 and an alpha value no higher than about 100, and as the hydrogenation component a minor amount of an added metal constituent comprising at least 50 weight percent of a component consisting of zinc and a metal from Group IB of the Periodic Table, e.g. copper, thereby converting the feedstock to aromatics.

15 Claims, No Drawings

PROCESS FOR CONVERTING C₂ TO C₈ ALIPHATICS TO AROMATICS OVER A METAL-ACTIVATED ZEOLITE

This is a continuation of copending application Ser. No. 905,101, filed on Sept. 8, 1986, and now abandoned.

BACKGROUND OF THE INVENTION

Field of the Invention

This invention relates to a process for the conversion of a gaseous feed containing a major proportion of $C_2$ to $C_8$ aliphatic hydrocarbons to aromatics in the presence of a crystalline zeolite catalyst containing a metal promotor comprising zinc and a metal from Group IB of the Periodic Table, e.g. copper.

Zeolites and alumina have been used in the past in the preparation of catalysts for the production of aromatic hydrocarbons from aliphatic hydrocarbons. The aliphatic hydrocarbon is passed over the catalyst at an elevated temperature in the liquid or vapor phase. Zeolites of various types have been suggested for the preparation of such catalysts. Examples of such zeolites are mordenite and the ZSM varieties, some of which contain zinc and a Group IB metal as ions which have been impregnated on the zeolite substrate or for which the original cations have been exchanged. However, it is desirable to improve the yields of aromatic hydrocarbons when using such catalysts.

U.S. Pat. No. 4,097,367 teaches the catalytic conversion of olefinic naphthas which contain diolefins over a special catalyst to yield a product stream which contains little or no non-aromatics boiling in the range of benzene, toluene and xylene. The catalyst is a combination of zinc and a metal from Groups IB and VIII of the Periodic Table with a crystalline aluminoscilicate zeolite having a silica-alumina ratio greater than 12 and a Constraint Index not less than one nor greater than 12.

U.S. Pat. No. 4,120,910 discloses that aromatic compounds can be produced by contacting, in the absence of added air or oxygen under suitable conversion conditions, a gaseous, paraffinic feed stock containing a high percentage of ethane with a ZSM-5 type crystalline aluminosilicate zeolite catalyst having incorporated therein a minor amount of a metal or metal oxide from Group VIII, IIB, or IB of the Periodic Table. Especially preferred is a zinc-copper mixture.

U.S. Pat. No. 4,350,835 teaches a catalytic process for converting a feedstock comprising a high percentage of ethane to aromatics employing as a catalyst a zeolite with a silica-alumina ratio of at least 12 and having incorporated therein a minor amount of gallium. The patent also discloses, for comparison purposes a catalyst containing 1% zinc and 0.25% copper supported on a ZSM-5 zeolite having a silica to alumina ratio of 40.

U.S. Pat. No. 4,392,989 shows the aromatization of paraffin feeds containing $C_2$-$C_{12}$ hydrocarbons using a catalyst comprising a zeolite containing zinc in combination with gallium or palladium, with the latter metal acting to retard or prevent the elution of zinc.

SUMMARY OF THE INVENTION

Briefly stated, this invention comprises a process for producing aromatic compounds including contacting under suitable conversion conditions a feed containing a major proportion of $C_2$-$C_8$ aliphatic hydrocarbons with a crystalline aluminosilicate zeolite catalyst having a relatively low acidity indicated by an alpha value no greater than about 100 and an added metal constituent comprising a major proportion of a component consisting of zinc and a metal from Group IB of the Periodic Table whereby a portion of the aliphatic compounds present in said feed is converted to aromatic compounds. It has been found that such a process results in a satisfactory degree of conversion of the feed hydrocarbons with relatively high selectivity to aromatics.

DESCRIPTION OF SPECIFIC EMBODIMENTS

Accordingly, the present invention is a process for producing aromatic hydrocarbons comprising bringing into contact at an elevated temperature a hydrocarbon feedstock containing a major proportion of $C_2$-$C_8$ aliphatic hydrocarbons with a catalyst composition comprising a zeolite having a relatively low acidity as indicated by an alpha value no greater than about 100, preferably no greater than about 60 and an added metal constituent comprising a major proportion of a component consisting of zinc and a metal from Group IB of the Periodic Table deposited thereon and/or whose cations have been exchanged with ions of said metal. Preferably, all of the added metal is the combination of zinc and copper as the Group IB metal.

As is known in the art, the acid catalytic activity of a zeolite may be measured by its "alpha value", which is the ratio of the rate constant of a test sample for cracking normal hexane to the rate constant of a standard reference catalyst, i.e. an amorphous silica alumina catalyst of 46 AI (Acidity Index). Thus, an alpha value = 1 means that the test sample and the standard reference have about the same activity. Thus alpha test is described in U.S. Pat. No. 3,354,078 and in *The Journal of Catalysis*, Vol. IV, pp. 527-529 (August 165), each incorporated as to that description. The relationship of alpha value to the intrinsic rate constants of other acid-catalyzed reactions is detailed in *Nature*, Vol. 309, pp. 589-591, June 14, 1984, incorporated herein by reference as to that detail.

The metal constituent comprising zinc and the Group IB metal in the catalyst composition may be deposited or impregnated onto the zeolite in which case it is usually present as oxides after calcination, or it may be present as ions if cations in the aluminosilicate support have been exchanged with ions of zinc and Group IB metal. In either case and particularly where the cations in the zeolite are exchanged for metal ions, the added metal constituent is suitably provided initially as an aqueous solution of metal salts such as for instance nitrates, sulfates, or chlorides. Thus, the catalyst may be produced by conventional ion exchange techniques and subsequently dried. For example, an aqueous solution of a compound of one or more metals of the added metal constituent such as a metal nitrate may be placed in contact with the zeolite at ambient or elevated temperature, e.g. by refluxing. The exhanged zeolite is then separated by decantation followed by filtration, washed several times with deionized water and finally dried. Before addition to the aqueous solution of the compound, the zeolite may be acid treated.

Whether impregnation or ion-exchange is used to add the metal constituent to the zeolite base, the zeolite may be initially treated simultaneously with solution of salts of all the metal components or serially with salts of individual metals. It has been found that for this application, it is advantageous to treat the zeolite serially with a metal salt solutions, e.g. with a solution of zinc nitrate followed by calcination and then with a solution of copper nitrate followed by calcination. The calcination for this purpose may be carried out at a temperature, for example, by heating the catalyst to about 450° to 600° C. at 1° C./min. and keeping it at that temperature for a period of about 1 to 10 hours.

Where the catalyst composition is prepared by using compounds of metals comprising zinc and Group IB metal which ionize in aqueous solution, for example zinc and Group IB metal nitrates, some of the metal ions are generally exchanged with the cations in the zeolite even if the preparation was directed to impregnation into the zeolite.

Whichever method of catalyst preparation is used, the amount of zinc plus Group IB metal present in the catalyst compositions, (metal plus zeolite) may vary for instance between about 0.5 and 20, preferably between about 1 and 10 percent by weight. Of the total amount of added metal, zinc plus Group IB metal may comprises an amount from over 50 to 100 wt.% and the zinc may comprise, for example about 25 to 95% by weight of the total of zinc and Group IB metal. The portion of the added metal, if any, which is not zinc or a Group IB metal may be any of various suitable metals in Groups I through VIII of the Periodic Table including by way of example palladium, platinum, rhenium, cobalt, tellurium, sodium, nickel, chromium, aluminum, gallium, titanium, tin, calcium and rare earth metals. Moreover, silver or gold may be used as the Group IB metal in place of copper.

The alpha value of a zeolite is an indication of its acidity and, for purposes of this invention is no higher than about 100. The zeolites of the desired alpha value or acidity can be obtained by controlling the silica-alumina ratios of the zeolite during synthesis or by steaming or high temperature treatment of a high acidity zeolite. Such alpha value decreases with a rise in the silica/alumina ratio of the zeolite and, in the absence of any specific treatment to reduce its acidity, the protonated or hydrogen form of the zeolite having an alpha value within the limits of this invention will generally have a silica/alumina ratio of at least 220. However, the acidity and thus the alpha value of a zeolite having a silica-alumina ratio below 220 may be reduced to the desired level by various means, e.g. steaming, high temperature treating or controlling the extent of protonation and coking. If such means are used to reduce below 100 the alpha value of a zeolite having a silica-alumina ratio of below 220, then such zeolite is contemplated for use in this invention. It should be noted also that since some acidity of the catalyst is necessary in order to obtain sufficient conversion of the feed hydrocarbons, the alpha value of the catalyst will in most cases be at least about 1.

The preferred method for reducing the acidity and thus the alpha value of an already formed zeolite having a set silica/alumina ratio is steaming which may be carried out for example, a temperature of about 700° to 1300° F. for a period of about 0.5 to 20,000 hours. For example, the time in hours required to steam a ZSM-5 zeolite with a silica/alumina ratio of 70 and initial alpha value of 220 at various temperatures and 1 atmosphere pressure to various levels of alpha value are shown below:

| Temp., °F. | Alpha Value of Steamed Zeolite | | |
|---|---|---|---|
| | 100 | 50 | 10 |
| 900 | 2 | 10 | 300 |
| 800 | 10 | 60 | 1500 |
| 700 | 80 | 400 | 11,000 |

The other preferred method for reducing the alpha value of a zeolite with an initially high alpha value to the desired level is by high temperature calcination in air or $N_2$, e.g. at a temperature of about 800° to 1000° C. for a period of about 1 to 10 hours. For example, a ZSM-5 zeolite with silica/alumina ratio of 70 and an alpha value of 220, may be calcined at 900° C. (1652° F.) for 1 and 2 hrs to obtain zeolites with alpha values of 80 and 50 respectively.

It has been discovered that the aromatization of light paraffins is a reaction catalyzed by acid/hydrogenation dual activity. These two acivity components of the catalyst should be balanced to obtain the optimum performance. If the relative acid/hydrogenation activity is higher than the optimum value, the catalyst cokes faster and the selectivity for aromatics decreases. On the other hand, if the relative acid/hydrogenation activity is lower than the optimum value, the catalyst shows lower conversion activity.

The hydrogenation activity of the catalyst can be varied by using different metal components. When the metal component is fixed, e.g. zinc and copper, the hydrogenation activity can be varied within a range by changing the metal content. As the metal content increases, the hydrogenation activity of the catalyst also increases. However, too high a content of metal could lead to plugging of the pores. As a result, only up to about 5 to 10 wt. % of zinc and copper may be used without any significant plugging of the pores and the acidity and the catalyst controlled to balance this hydrogenation activity. Put another way, there is a limitation on the use of metal content in controlling the hydrogenation activity of the catalyst and the acidity must therefore be controlled to balance the hydrogenation activity, which means acidity reduction in most cases.

Since the best catalyst performance is achieved when the acidity and hydrogenation activities are balanced, it has also been determined that the optimum acidity of a catalyst as indicated by its alpha value is dependent on its zinc content and, in turn, the hydrogenation activity of the catalyst. Thus, at a zinc content of 1 to 4% by weight of the catalyst, the alpha value is preferably in the range of about 5 to 60, with said value preferably being in the range of about 5 to 20 at a 1% by weight zinc content, and about 20 to 60 at a 4% by weight zinc content, and the limits of the ranges of alpha values at zinc contents between 1 and 4 wt. % being in a linear relationship with the limits of said ranges at 1 and 4% by weight zinc content.

Although the zeolites utilized in the process generally have low alumina contents, i.e. silica to alumina mole ratios exceeding 220 in the absence of any treatment to reduce their acidity, they are nevertheless very active. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning in air to restore activity. These zeolites, used as catalysts, generally have low coke-forming tendency and therefore are conducive to long times on stream between regenerations by burning carbonaceous deposits with oxygen-containing gas such as air.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with silica to alumina mole ratios of at least 220 and in some cases lower, are useful, it is preferred in some instances to use zeolites having substantially higher silica/alumina ratios, e.g. 1600 and above. Such "high-silica" or highly siliceous" zeolites are intended to be included within this description, as long as the alpha value or acidity is sufficient for the particular application. It has also been found that zeolites with too high a silica/alumina ratio in the framework and too low an alpha value can be activated with external alumina by impregnation/calcination or $NH_4OH$ treating to increase the alpha value to the desired level.

The members of the class of zeolites useful herein have an effective pore size of generally from about 5 to about 8 angstroms, such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolites is not of the desired type. Windows of 10-membered rings are preferred, although, in some instances, excessive puckering of the rings or pore blockage may render these zeolites ineffective.

Although 112-membered rings in theory would not offer sufficient constraint to produce advantageous conversions, it is noted that the puckered 12-ring structure of TMA offretite does show some constrained access. Other 12-ring structures may exist which may be operative for other reasons, and therefore, it is not the present intention to entirely judge the usefulness of the particular zeolite solely from theoretical structural considerations.

A convenient measure of the extent to which a zeolite provides control to molecules of varying sizes to its internal structure is the Constraint Index of the zeolite. Zeolites which provide a highly restricted access to and egress from its internal structure have a high value for the Constraint Index, and zeolites of this kind usually have pores of small size, e.g. less than 5 angstroms. On the other hand, zeolites which provide relatively free access to the internal zeolite structure have a low value for the Constraint Index, and usually pores of large size, e.g. greater than 8 angstroms. The method by which Constraint Index is determined is described fully in U.S. Pat. No. 4,016,218, incorporated herein by reference for details of the method.

Constraint Index (CI) values for some typical materials are:

|  | CI | (at test temperatures) |
| --- | --- | --- |
| ZSM-4 | 0.5 | (316° C.) |
| ZSM-5 | 6–8.3 | (371° C.–316° C.) |
| ZSM-11 | 5–8.7 | (371° C.–316° C.) |
| ZSM-12 | 2.3 | (316° C.) |
| ZSM-20 | 0.5 | (371° C.) |
| ZSM-22 | 7.3 | (427° C.) |
| ZSM-23 | 9.1 | (427° C.) |
| ZSM-34 | 50 | (371° C.) |
| ZSM-35 | 4.5 | (454° C.) |
| ZSM-38 | 2 | (510° C.) |
| ZSM-48 | 3.5 | (538° C.) |
| ZSM-50 | 2.1 | (427° C.) |
| TMA Offretite | 3.7 | (316° C.) |
| TEA Mordenite | 0.4 | (316° C.) |
| Clinoptilolite | 3.4 | (510° C.) |
| Mordenite | 0.5 | (316° C.) |
| REY | 0.4 | (316° C.) |
| Amorphous Silica-alumina | 0.6 | (538° C.) |
| Dealuminized Y | 0.5 | (510° C.) |
| Erionite | 38 | (316° C.) |
| Zeolite Beta | 0.6–2.0 | (316° C.–399° C.) |

The above-described Constraint Index is an important and even critical definition of these zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operations (conversion) and the presence or absence of binders. Likewise, other variables, such as crystal size of the zeolite, the presence of occluded contaminants, etc., may affect the Constraint Index. Therefore, it will be appreciated that it may be possible to so select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites, but that such are the cumulative result of several variables useful in the determination and calculation thereof. Thus, for a given zeolite exhibiting a CI value within the range of 1 to 12, depending on the temperature employed during the test method within the range of 290° C. to about 538° C., with accompanying conversion between 10% and 60%, the CI may vary within the indicated range of 1 to 12. Likewise, other variables such as the crystal size of the zeolite, the presence of possibly occluded contaminants and binders intimately combined with the zeolite may affect the CI. It will accordingly be understood to those skilled in the art that the CI, as utilized herein, while affording a highly useful means for characterizing the zeolites of interest is approximate, taking into consideration the manner of its determination, with the possibility, in some instances, of compounding variable extremes. However, in all instances, at a temperature within the above-specified range of 290° C. to about 538° C., the CI will have a value for any given zeolite of interest herein within the approximate range of 1 to 12.

The class of zeolites defined herein is exemplified by ZSM-5, ZSM-11, ZSM-12, ZSM-23, ZSM-35, ZSM-38, ZSM-48, and other similar materials. The compositions, methods of preparation, and X-ray diffraction patterns of these zeolites are typified in the following patents: ZSM-5 in U.S. Pat. No. 3,702,886 and Re. No. 29,948; ZSM-11 in U.S. Pat. No. 3,709,979; ZSM-12 in U.S. Pat.

No. 3,832,449; ZSM-23 in U.S. Pat. No. 4,076,842; ZSM-35 in U.S. Pat. No. 4,016,245; ZSM-38 in U.S. Pat. No. 4,046,859 and ZSM-48 in U.S. Pat. No. 4,350,835. The entire disclosures of these patents are incorporated by reference insofar as their disclosures are necessary to identify the respective zeolites.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is in many cases is at least 220 and may be as high as about 5000. As stated, zeolites having an as synthesized silica/alumina ratio of less than 220 may also be used, but for these zeolites, treatment such as steaming is required to reduce its acid activity to an alpha value of no higher than about 100. In any case, the incorporation of the identified patents should not be construed as limiting the disclosed crystalline zeolites to those having the specific silica-alumina mole ratios discussed therein, it now being known that such zeolites may have much higher silica-alumina ratios and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at about 540° C. for one hour, for example, followed by base exchange with ammonium salts followed by calcination at about 540° C. in air. The presence of organic cations in the forming solution may not be absolutely essential to the formation of this type zeolite; however, the presence of these cations does appear to favor the formation of this special class of zeolite. In many cases, it is desirable to activate this type catalyst by base exchange with ammonium salts followed by calcination in air at about 538°–540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38 and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, an alpha value no higher than about 100, a silica to alumina mole ratio of at least about 220 in the absence of treatment to reduce its acidity and up to about 5000, and a dried crystal density of not less than about 1.6 grams per cubic centimeter. The dry density for known structures may be calculated from the number of silicon plus aluminum atoms per 1000 cubic angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with zinc and a Group IB metal and, if desired other suitable metal cations, of Groups I through VII of the Periodic Table as mentioned previously.

In practicing a particularly desired chemical conversion process, it may be useful to incorporate the above-described crystalline zeolite with a matrix comprising another material resistant to the temperature and other conditions employed in the process. Such matrix material is useful as a binder and imparts greated resistance to the catalyst for the severe temperature, pressure and reactant feed stream velocity conditions encountered in many conversion processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Alumina, however, should be avoided. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, kickite, nacrite or anauxite. Such clays can be used in the raw state as originally mined or initially subjected to calcination, acid treatment or chemical modification.

In addition to the foregoing materials, the zeolites employed herein may be composited with a porous inorganic oxide matrix material for forming into the desired shape and size by extrusion and pelleting. Such matrix materials may be, for example, those comprising silica, e.g. silica itself, silica-magnesia, silica-zirconia, silica-thoria, silica-beryllia, and silica-titania, as well as ternary compositions, such as silica-magnesia-zirconia. The preferred matrix material is silica. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite. Methods for binding the catalysts of this invention are further described in U.S. Pat. No. 4,582,815 issued Apr. 15, 1986 to E. Bowes.

The feed stream to the process of this invention contains at least 50% by weight of at least one aliphatic hydrocarbon containing 2 to 8 carbon atoms. The hydrocarbon may be straight chain, open chain or cyclic and may be saturated or unsaturated. Some contemplated hydrocarbons are ethane, ethylene, propane, propylene, n-butane, n-butenes, isobutane, isobutene, straight-and branch chain pentanes, pentenes, hexanes, hexenes, heptanes, heptenes, octanes, and octenes, and cycloaliphatic hydrocarbons such as cyclohexane and cyclohexene, and raffinates ($C_6$, $C_7$) from aromatic extraction processes. Dienes may also be present but should not exceed about 70% by weight of the feed. The process is particularly suitable for producing additional aromatics from low value gases, e.g. refinery fuel gases such as light gases from catalytic crackers, cokers, visbreakers, steam crackers, and distillation towers, and normally gaseous natural gas condensates.

The process of this invention is conducted so that a feed containing a high percentage, i.e. at least 50 wt. % of $C_2$-$C_8$ aliphatic hydrocarbons is contacted with a suitable zeolite catalyst in a reaction zone, e.g. a cyclic fixed bed reactor, a moving bed reactor or a fluidized bed reactor. When a fluidized bed reactor is used, baffle plates should be used to reduce the back mixing. The process maybe carried out at, for example, at a temperature of about 800° to 1200° F., preferably about 900° to 1050° F., a pressure of about 0 to 2000 psig, preferably about 5 to 500 psig, and a feed weight space velocity (WHSV) of about 0.01 to 200, preferably about 0.05 to 20. The desired conversion level is about 10 to 100% per pass, preferably about 30 to 95% per pass. In general, the optimum ranges of conditions will vary depending on the nature of the feedstocks, with higher temperatures of reaction being more desirable with lighter feedstocks, e.g. ethane, and lower temperatures of reaction being desirable for heavier feedstocks, e.g. propane and hexane.

The effluent from the reaction zone is separated and distilled to remove the desired aromatic product and the remainder is recycled for further reaction or for use as fuel gas.

The following examples further illustrate the invention. Examples 1 to 57 are embodiments of processes carried out within the invention, while Comparative Examples A to F are similar embodiments which show the results obtained when at least one parameters is outside the scope of the invention.

In carrying out these examples, feed gases of high quality commercial grades were used directly without purification. The reactor was a ⅜" stainless steel tubing with thermowell at the center. Four cc (3.3 g) of the catalyst was packed into the reactor in 4 zones, each sandwiched with 0.5 cc of fine quartz. The feed was started when the reactor reached bout 250° C. without catalyst pretreating. The total effluent was analyzed with an on line gas chromatography.

The product yields in wt. %, were divided by the fractional conversion of the feed hydrocarbon or a specified intermediate to obtain the product selectivity in wt. %. The product selectivities for benzene, toluene and xylenes (BTX) and aromatic $C_9$'s were obtained by adding up the individual selectivities.

EXAMPLES 1 AND 2 AND COMPARATIVE EXAMPLES, A, B AND C

These examples illustrate the aromatization of propane using the process of this invention.

The catalysts used were prepared from the sodium form of a ZSM-5 zeolite having a silica/alumina ratio of 880 in Examples 1 and 2 and 70 in Comparative Examples A, B and C. The zeolite was calcined in $N_2$ at 1° C./min to 538° C. and kept at 538° C. for 3 hrs. The catalyst was then ion exchanged three times with 5 cc/g of 1 N $NH_4NO_3$ for 30 min. each, and finally calcined in air at 1° C./min to 538° C. and kept at 538° C. for 3 hrs. The resulting hydrogen form (HZSM-5) of the zeolite was impregnated with 1% Zn using $ZN(NO_3)_2$ solution and then calcined in air at 538° C. The product was then impregnated with 1% Cu using Cu $(NO_3)_2$ and finally calcined in air at 538° C.

The aromatization reaction was carried at a temperature of 1000° F. and a pressure of 20 psig. The silica/alumina ratios and alpha values of the catalysts, propane flow rates and results of the aromatization reactions are shown in Table I:

TABLE I

| Example | 1 | 2 | A | B | C |
|---|---|---|---|---|---|
| Silica/alumina Ratio | 880 | 880 | 70 | 70 | 70 |
| Alpha Value | 5 | 5 | 250 | 250 | 250 |

TABLE I-continued

| Example | 1 | 2 | A | B | C |
|---|---|---|---|---|---|
| C$_3$ Flow Rate, cc/mm | 144 | 36 | 576 | 288 | 72 |
| Conversion to C$_2$ and lighter, wt. % | 23.6 | 40.0 | 25.9 | 47.0 | 65.2 |
| Aromatics Selectivity, % | 85.6 | 78.3 | 56.1 | 57.1 | 55.9 |

The results of these examples show that there is a a trend toward higher aromatic selectivities when the alpha value of the catalyst is reduced from a value over 100 to a value under 100, and in the case of untreated catalysts, when the silica/alumina ratio rises from a value under 220 to a value over 220.

EXAMPLES 3 TO 11

These examples illustrate the aromatization of propane (Examples 3 to 10) and hexane (Example 11) under the process of this invention using varying process conditions. The catalyst containing 1 wt. % of zinc and 1 wt. % of copper was prepared as described in Examples 1 and 2 except that the sodium ZSM-5 had a silica/alumina ratio of about 520 and the hydrogen ZSM-5 had an alpha value of about 14. The pressure of reaction was 20 psig. the propane space velocity in Examples 3 to 10 was 270 cc/cc hr (GHSV) and the hexane space velocity in Example 11 was 4 cc/cc hr (LHSV). Other process conditions and the results of the reaction are shown in Table II, where "C$_9$A" indicates nine carbon aromatics:

TABLE II

| Example | 3 | 4 | 5 | 6 | 7 | 8 | 9 | 10 | 11 |
|---|---|---|---|---|---|---|---|---|---|
| Temp, °F. | 1000 | 1000 | 1050 | 1050 | 1000 | 1000 | 1022 | 1022 | 1000 |
| On Stream Time, hr | 5.00 | 5.50 | 7.00 | 75.50 | 47.50 | 55.00 | 120.00 | 123.00 | 60.00 |
| Conversion, wt. % | 33.68 | 33.51 | 48.85 | 48.16 | 44.07 | 31.12 | 31.54 | 26.74 | 95.30 |
| Product Analysis, H$_2$ free basis Wt. % | | | | | | | | | |
| Methane | 3.81 | 3.40 | 4.75 | 4.63 | 3.00 | 2.53 | 2.86 | 2.67 | 1.94 |
| Ethylene | 1.29 | 1.34 | 2.25 | 2.20 | 1.63 | 2.17 | 2.10 | 2.23 | 2.53 |
| Ethane | 4.18 | 3.68 | 4.61 | 4.53 | 3.20 | 1.77 | 2.42 | 2.01 | 3.61 |
| Propane (Feed) | 66.32 | 66.49 | 51.15 | 51.84 | 55.93 | 68.88 | 68.46 | 73.25 | 6.29 |
| Butenes | — | — | — | — | 0.46 | 0.51 | 0.48 | 0.47 | 2.33 |
| Butanes | — | — | 0.48 | 0.40 | 0.56 | 0.48 | 0.49 | 0.45 | 2.82 |
| C$_5$'s | — | — | — | — | 0.15 | 0.19 | 0.17 | 0.17 | 0.82 |
| Benzene | 7.28 | 7.15 | 10.58 | 10.38 | 8.67 | 6.35 | 6.42 | 5.83 | 10.21 |
| Toluene | 12.17 | 13.11 | 15.06 | 14.80 | 12.68 | 9.63 | 8.46 | 7.64 | 24.30 |
| Xylenes | 4.95 | 4.83 | 11.22 | 11.22 | 10.02 | 6.39 | 5.83 | 4.95 | 25.10 |
| C$_9$A | | | | 3.71 | 1.09 | 2.30 | 0.31 | 11.57 | |
| Propylene | | | | | | | | 3.83 | |
| Hexane | | | | | | | | 4.71 | |
| Product Selectivity, % | | | | | | | | | |
| Aromatics | 72.45 | 74.87 | 75.46 | 75.58 | 79.60 | 75.97 | 72.95 | 69.04 | 74.69 |
| C$_1$ + Ethane | 23.72 | 21.13 | 19.16 | 19.02 | 14.07 | 13.82 | 16.74 | 17.51 | 5.83 |

The results of Table II show that relatively high aromatics selectivities can be obtained with reasonable conversion rates using the process of this invention. pcl

EXAMPLES 12 TO 14 AND COMPARATIVE EXAMPLES D, E AND F

These examples further illustrate the importance of using a catalyst prepared from a zeolite of relatively low acidity as indicated by an alpha number of under 100, in obtaining high aromatics selectivity in the aromatization of propane.

The catalysts containing 1 wt. % zinc and 1 wt. % copper were prepared as described in Examples 1 and 2 except that the catalyst of Examples 12 to 14 was prepared from a zeolite having a silica/alumina ratio of 285 and an alpha value of 79.2 while that of Comparative Examples D, E and F had a silica/alumina ratio of 70 and an alpha value of 250. The pressure of reaction was 20 psig. Other conditions of reaction and the results are shown in Table III:

TABLE III

| Example | D | E | F | 12 | 13 | 14 |
|---|---|---|---|---|---|---|
| SiO$_2$/Al$_2$O$_3$ Ratio | 70 | 70 | 70 | 285 | 285 | 285 |
| Alpha Value | 250 | 250 | 250 | 79.2 | 79.2 | 79.2 |
| Temp, °F. | 1000 | 1000 | 1000 | 1011 | 1000 | 954 |
| WHSV, g/g hr | 0.27 | 1.08 | 2.16 | 1.08 | 1.08 | 1.50 |
| On Stream Time, hr | 1.5 | 2 | 4 | 0.5 | 1.0 | 3.5 |
| Conversion, wt % | 99.62 | 99.33 | 99.53 | 85.31 | 86.73 | 75.46 |
| Product Yield, wt % (H$_2$ free basis) | | | | | | |
| Methane | 17.92 | 14.54 | 20.01 | 6.71 | 6.74 | 5.79 |
| Ethylene | 0.52 | 0.47 | 0.56 | 0.96 | 1.01 | 0.81 |
| Ethane | 29.00 | 29.66 | 35.61 | 19.32 | 19.09 | 17.07 |
| Propylene | 0.06 | 0.09 | 0.00 | 1.61 | 1.32 | 0.00 |
| Propane (Feed) | 0.38 | 0.67 | 0.47 | 14.69 | 13.27 | 24.54 |
| Butenes | 0.00 | 0.00 | 0.00 | 0.24 | 0.19 | 0.78 |
| Butanes | 0.00 | 0.00 | 0.00 | 0.37 | 0.29 | 1.45 |
| C$_5$'s | 0.00 | 0.00 | 0.00 | 0.04 | 0.03 | 0.13 |
| Benzene | 18.36 | 12.59 | 16.56 | 15.92 | 15.53 | 13.61 |
| Toluene | 22.52 | 17.83 | 20.05 | 17.42 | 17.08 | 16.07 |
| Xylenes | 9.97 | 9.21 | 6.71 | 13.47 | 14.98 | 15.33 |
| C$_9$A | 1.29 | 0.00 | 0.00 | 9.23 | 10.54 | 4.42 |
| Product Selectivity, % | | | | | | |
| Aromatics | 52.3 | 39.9 | 43.5 | 65.7 | 66.9 | 65.5 |
| C$_4$ & C$_5$'s | 0.0 | 0.0 | 0.0 | 1.2 | 0.6 | 3.1 |
| C$_1$ & Ethane | 47.1 | 44.5 | 55.9 | 30.5 | 29.8 | 30.3 |

The results of Table III again show that higher aromatic selectivities are obtained when the catalyst is prepared from a zeolite of relatively low acidity as indicated by an alpha value of under 100.

EXAMPLES 15 TO 21

These examples illustrate the effect of acidity as indicated by alpha value of zeolites used to prepare catalysts within the scope of the invention.

The procedure of the previous examples for the preparation of a catalyst containing 1 wt% of zinc and 1% of copper and the aromatization of propane was followed with the ZSM-5 zeolite used to prepare the catalyst having a silica/alumina ratio of 520 and an alpha value of 39.5 in Examples 15 to 18 and a silica/alumina ratio of 965 and an alpha value of 3.3 in Examples 19 to 21. The conditions and results of the reactions of these examples are shown in Table IV:

TABLE IV

| Example | 15 | 16 | 17 | 18 | 19 | 20 | 21 |
|---|---|---|---|---|---|---|---|
| $SiO_2/Al_2O_3$ | 520 | 520 | 520 | 520 | 965 | 965 | 965 |
| Alpha Value | 39.5 | 39.5 | 39.5 | 39.5 | 3.3 | 3.3 | 3.3 |
| Temp, °F. | 1000 | 1000 | 1000 | 988 | 1011 | 1011 | 1070 |
| WHSV, g/g hr | 0.27 | 1.08 | 2.16 | 0.27 | 0.54 | 4.16 | 3.6 |
| On Stream Time, hr | 2.5 | 4.5 | 5.5 | 95.5 | 2.3 | 5.1 | 6.5 |
| Conversion, wt % | 90.69 | 69.3 | 56.89 | 83.40 | 67.38 | 47.87 | 62.93 |
| Product Yield, wt % ($H_2$ free basis) | | | | | | | |
| Methane | 12.75 | 10.26 | 6.21 | 4.60 | 3.71 | 2.68 | 3.84 |
| Ethylene | 0.46 | 0.66 | 0.67 | 0.72 | 2.40 | 3.16 | 3.37 |
| Ethane | 28.04 | 23.16 | 13.81 | 12.89 | 9.02 | 4.05 | 7.26 |
| Propylene | 0.66 | 1.35 | 0.00 | 0.00 | 0.0 | 0.0 | 0.0 |
| Propane (Feed) | 9.31 | 30.70 | 43.11 | 16.64 | 32.62 | 52.13 | 37.97 |
| Butenes | 0.00 | 0.34 | 0.46 | 0.33 | 1.37 | 1.98 | 1.63 |
| Butanes | 0.12 | 0.58 | 0.77 | 0.57 | 1.47 | 1.49 | 1.54 |
| $C_5$'s | 0.00 | 0.00 | 0.10 | 0.06 | 0.41 | 0.63 | 0.57 |
| Benzene | 17.04 | 14.02 | 11.01 | 12.84 | 11.97 | 7.04 | 10.54 |
| Toluene | 21.77 | 14.26 | 15.29 | 14.53 | 23.04 | 9.69 | 22.15 |
| Xylenes | 9.08 | 4.69 | 8.21 | 21.77 | 9.91 | 9.27 | 8.29 |
| $C_9A$ | 0.77 | 0.00 | 0.36 | 11.27 | 1.69 | 7.88 | 3.74 |
| Product Selectivity, % | | | | | | | |
| Aromatics | 53.7 | 47.6 | 61.3 | 72.5 | 69.2 | 70.8 | 71.06 |
| $C_4$ & $C_5$'s | 0.1 | 0.8 | 1.5 | 1.2 | 4.8 | 9.6 | 6.0 |
| $C_1$ & Ethane | 45.0 | 48.2 | 35.2 | 21.0 | 18.9 | 14.5 | 17.6 |

The results of Table IV indicate that under equivalent process conditions including on stream times, the use of catalysts prepared from zeolites of higher silica/alumina ratio and therefore having lower acidity as indicated by alpha value, generally result in higher aromatics selectivities. The relatively high aromatics selectivity and propane conversion obtained in Example 18 wherein the silica/alumina ratio was 520 is probably related to the high on stream time of that example.

EXAMPLES 22 TO 29

These examples illustrate the effectiveness of steaming to reduce the acidity and thus the alpha value of a catalyst prepared from a zeolite having the relatively low silica/alumina ratio of 70. Although catalysts prepared from this zeolite initially had too high an alpha value to be within the scope of the invention, the steam treatment substantially reduced its alpha value so that it was brought within the invention.

The procedure of the previous examples for the preparation of a catalyst containing 1 wt. % of zinc and 1 wt. % of copper, and the aromatization of propane was followed with the silica/alumina ratio of the zeolite being 70 in Examples 22 to 27 and 520 in Examples 28 and 29 and all the zeolites after the ammonium exchange being subjected to a steaming treatment at 1000° F. for 72 hours, resulting in the catalysts of Examples 22 to 25 having an alpha value of 7.0 and those of Examples 26 to 29 having an alpha value of 9.0. The conditions and results of these examples are shown in Table V:

TABLE V

| Example | 22 | 23 | 24 | 25 | 26 | 27 | 28 | 29 |
|---|---|---|---|---|---|---|---|---|
| $SiO_2/Al_2O_3$ | 70 | 70 | 70 | 70 | 70 | 60 | 520 | 520 |
| Alpha Value | 7.0 | 7.0 | 7.0 | 7.0 | 9.0 | 9.0 | 9.0 | 9.0 |
| Temp, °F. | 988 | 988 | 977 | 894 | 1000 | 1000 | 1050 | 1050 |
| WHSV, g/g hr | 0.27 | 0.27 | 4.32 | 1.08 | 0.27 | 0.27 | 0.27 | 0.27 |
| On Stream Time, hr | 1.5 | 3 | 4.8 | 22.5 | 5.0 | 6.0 | 8.0 | 24.5 |
| Conversion, wt % | 79.24 | 82.36 | 68.62 | 77.03 | 33.68 | 33.51 | 48.85 | 48.16 |
| Product Yield, wt % ($H_2$ free basis) | | | | | | | | |
| Methane | 12.70 | 8.36 | 4.83 | 6.36 | 3.81 | 3.40 | 4.75 | 4.63 |
| Ethylene | 0.57 | 2.07 | 3.69 | 2.03 | 1.29 | 1.34 | 2.25 | 2.20 |
| Ethane | 11.64 | 17.35 | 9.80 | 15.50 | 4.18 | 3.68 | 4.61 | 4.53 |
| Propylene | 0.0 | 0.94 | 0.0 | 0.0 | 0.00 | 0.00 | 0.00 | |
| Propane (Feed) | 20.76 | 17.64 | 31.38 | 22.97 | 66.32 | 66.49 | 51.15 | 51.84 |
| Butenes | 0.08 | 0.14 | 0.74 | 0.39 | 0.00 | 0.00 | 0.00 | 0.00 |
| Butanes | 0.12 | 0.17 | 0.90 | 0.48 | 0.00 | 0.00 | 0.38 | 0.40 |
| $C_5$'s | 0.03 | 0.0 | 0.30 | 0.17 | 0.00 | 0.00 | 0.00 | |
| Benzene | 13.43 | 13.46 | 12.22 | 15.33 | 7.28 | 7.15 | 10.58 | 10.38 |
| Toluene | 29.01 | 34.46 | 27.77 | 26.32 | 12.17 | 12.17 | 13.11 | 15.06 |
| Xylenes | 7.66 | 2.93 | 6.30 | 4.51 | 4.95 | 4.83 | 11.22 | 11.22 |
| $C_9A$ | 4.01 | 2.48 | 2.03 | 5.93 | 0.0 | | | |
| Product Selectivity, % | | | | | | | | |
| Aromatics | 68.3 | 64.8 | 70.4 | 67.6 | 72.5 | 74.9 | 74.4 | 74.6 |
| $C_4$ & $C_5$'s | 0.3 | 0.4 | 2.8 | 1.4 | 0.0 | 0.0 | 0.0 | 0.0 |
| $C_1$ & Ethane | 30.7 | 31.2 | 21.3 | 28.4 | 23.7 | 21.1 | 19.2 | 19.0 |

The results of Table V show that when the alpha value of a catalyst prepared from a zeolite with a silica/alumina ratio of 70 was substantially reduced by steaming, relatively high aromatics selectivities were obtained. Furthermore, such selectivities were comparable to those obtained with the catalysts prepared from a steam treated zeolite having a silica/alumina ratio of 520 and an alpha value of 9.0, utilized in Examples 28 and 29.

EXAMPLES 30 TO 33

These examples illustrate the effect of employing a catalyst within the scope of the invention having a relatively high zinc content.

The procedure of the preceding examples for the aromatization of propane was followed with the catalyst being prepared from a ZSM-5 zeolite having a silica/alumina ratio of 520 and an alpha value of 55.8 and the zinc and copper nitrates impregnation steps were carried out such that the catalyst contained 4 wt. % of zinc and 1 wt. % of copper. The conditions and results of these examples are shown in Table VI.

TABLE VI

| Example | 30 | 31 | 32 | 33 |
|---|---|---|---|---|
| Temp, °F. | 986 | 988 | 984 | 997 |
| WHSV, g/g hr | 0.27 | 0.27 | 0.08 | 0.27 |
| On Stream Time, hr | 2 | 10 | 33 | 34.2 |

TABLE VI-continued

| Example | 30 | 31 | 32 | 33 |
|---|---|---|---|---|
| Conversion, wt % | 78.59 | 83.2 | 68.57 | 93.49 |
| Product Yield, wt % (H$_2$ free basis) | | | | |
| Methane | 5.63 | 5.95 | 4.35 | 6.52 |
| Ethylene | 0.63 | 1.23 | 2.16 | 1.03 |
| Ethane | 12.63 | 15.98 | 11.13 | 17.46 |
| Propylene | 1.62 | 2.60 | 0.0 | 0.74 |
| Propane (Feed) | 2.141 | 16.80 | 31.43 | 6.51 |
| Butenes | 1.21 | 0.36 | 1.14 | 0.07 |
| Butanes | 0.79 | 0.54 | 1.58 | 0.11 |
| C$_5$'s | 0.19 | 0.13 | 0.34 | 0.06 |
| Benzene | 10.06 | 17.43 | 12.89 | 16.12 |
| Toluene | 13.12 | 25.79 | 14.73 | 20.38 |
| Xylenes | 14.92 | 9.36 | 12.59 | 27.13 |
| C$_9$A | 17.23 | 3.82 | 7.67 | 3.87 |
| Product Selectivity, % | | | | |
| Aromatics | 70.39 | 66.8 | 69.8 | 72.2 |
| C$_4$ & C$_5$'s | 2.8 | 1.2 | 4.5 | 0.2 |
| C$_1$ & Ethane | 23.2 | 26.4 | 22.6 | 25.7 |

The results of Table VI indicate that the use of a catalyst containing a relatively large amount of zinc, viz. 4 wt. %, effected high aromatics selectivities at particularly high propane conversion rates.

EXAMPLES 34 TO 37

These examples illustrate the effect of space velocity on the results obtained with catalysts containing 1 wt. % and 4 wt. % of zinc.

The procedure of the preceding examples for the aromatization of propane was followed with catalysts containing 1% copper and either 1% zinc (Examples 34 and 35) or 4 wt. % of zinc (Examples 36 and 37). The conditions and results of the examples are shown in Table VII:

TABLE VII

| Example | 34 | 35 | 36 | 37 |
|---|---|---|---|---|
| Zn % | 1.0 | 1.0 | 4.0 | 4.0 |
| Cu % | 1.0 | 1.0 | 1.0 | 1.0 |
| Alpha Value | 39.5 | 39.5 | 55.8 | 55.8 |
| Temp, °F. | 1000 | 1000 | 986 | 984 |
| WHSV, g/g hr | 0.27 | 2.2 | 0.3 | 1.1 |

TABLE VII-continued

| Example | 34 | 35 | 36 | 37 |
|---|---|---|---|---|
| On Stream Time, hr. | 2.5 | 5.5 | 2.0 | 33.0 |
| Conversion, wt % | 90.7 | 56.9 | 78.6 | 68.6 |
| Product Yield, wt % | | | | |
| Methane | 12.75 | 6.21 | 5.63 | 4.35 |
| Ethylene | 0.46 | 0.67 | 0.63 | 2.16 |
| Ethane | 28.04 | 13.81 | 12.63 | 11.13 |
| Propylene | 0.66 | 0.00 | 1.62 | 0.00 |
| Propane (Feed) | 9.31 | 43.11 | 21.41 | 31.43 |
| Butenes | 0.00 | 0.46 | 1.21 | 1.14 |
| Butanes | 0.12 | 0.77 | 0.79 | 1.58 |
| C$_5$'s | 0.00 | 0.10 | 0.19 | 0.34 |
| Benzene | 17.04 | 11.01 | 10.16 | 12.89 |
| Toluene | 21.77 | 15.29 | 13.12 | 14.73 |
| Xylenes | 9.08 | 8.21 | 14.92 | 12.59 |
| C$_9$A | 0.77 | 0.36 | 17.23 | 7.67 |
| Product Selectivity, % | | | | |
| Aromatics | 53.7 | 61.3 | 70.4 | 69.8 |
| C$_4$ & C$_5$'s | 0.1 | 1.5 | 2.8 | 4.5 |
| C$_1$ & Ethane | 45.0 | 35.2 | 23.2 | 22.6 |
| C$_2$= | 0.5 | 1.2 | 0.8 | 3.1 |

The results of Table VII show that the conversion of feed hydrocarbon is inversely proportional to the space velocity and that a higher percentage of zinc in the catalyst results higher aromatics selectivities, within the operable limits of the process.

EXAMPLES 38 TO 44

These examples illustrate the process of this invention used for the aromatization of ethane.

The procedure of the preceding examples was followed, with the feed hydrocarbon being ethane and the catalyst containing 4 wt. % of zinc and 1 wt. % of copper on a ZSM-5 zeolite having a silica/alumina ratio of 520 and an alpha value of 55.8, bound with 15% silica. The conditions and results of these examples are shown in Table VIII:

TABLE VIII

| Example | 38 | 39 | 40 | 41 | 42 | 43 | 44 |
|---|---|---|---|---|---|---|---|
| Temp, °F. | 997 | 996 | 1065 | 1065 | 1065 | 1065 | 1065 |
| WHSV, g/g hr | 1.8 | 1.8 | 1.8 | 1.8 | 3.6 | 7.2 | 7.2 |
| On Stream Time, hr | 119.8 | 120.5 | 121.3 | 121.5 | 123.7 | 122.5 | 123.0 |
| Conversion, wt % | 46.1 | 43.7 | 53.2 | 53.9 | 35.7 | 23.0 | 23.8 |
| Product Yield, wt % (H$_2$ free basis) | | | | | | | |
| Methane | 0.76 | 0.80 | 2.20 | 2.50 | 0.48 | 0.11 | 0.11 |
| Ethylene | 11.18 | 11.69 | 11.40 | 11.32 | 16.66 | 18.61 | 18.63 |
| Ethane | 53.87 | 56.34 | 46.80 | 47.03 | 63.31 | 76.99 | 76.20 |
| Propylene | 0.77 | 0.81 | 1.25 | 1.27 | 0.80 | 0.17 | 0.17 |
| Propane (Feed) | 1.06 | 1.11 | 1.65 | 1.78 | 0.38 | 0.03 | 0.03 |
| Butenes | 0.53 | 0.55 | 0.60 | 0.58 | 0.89 | 0.39 | 0.39 |
| Butanes | 0.66 | 0.68 | 0.68 | 0.68 | 0.91 | 0.40 | 0.40 |
| C$_5$'s | 0.11 | 0.10 | 0.21 | 0.10 | — | 0.05 | — |
| Benzene | 5.71 | 5.61 | 9.45 | 9.92 | 3.24 | 1.24 | 0.41 |
| Toluene | 6.93 | 7.69 | 10.90 | 10.25 | 4.27 | 2.01 | 2.04 |
| Xylene | 10.98 | 6.69 | 9.41 | 6.61 | 3.63 | — | — |
| C$_9$A | 0.77 | 0.00 | 0.36 | 11.27 | 1.69 | 7.88 | 3.74 |
| Product Selectivity, % | | | | | | | |
| Aromatics | 66.5 | 63.9 | 66.2 | 65.6 | 44.8 | 14.1 | 17.1 |
| C$_4$, C$_5$ | 2.8 | 3.1 | 2.7 | 2.6 | 4.9 | 2.1 | 3.3 |
| C$_3$= | 1.7 | 1.9 | 2.4 | 2.4 | 2.2 | 0.7 | 0.7 |
| C$_2$= | 23.9 | 26.8 | 21.4 | 21.4 | 45.4 | 80.9 | 78.3 |
| C$_1$= | 1.6 | 1.8 | 4.1 | 4.7 | 1.3 | 0.5 | 0.5 |

The results of Table VIII show that ethane can be aromatized at relatively high overall conversion rates and aromatics selectivities by means of the process of this invention. As expected, the conversion and aromatics selectivity are lower per pass at higher space velocity. However, this is accompanied by higher yields of ethylene which is an aromatics precursor so that the overall aromatics yields with recycle are comparable at a wide range of space velocities.

EXAMPLES 45 TO 57

These examples illustrate the use of catalysts containing varying amounts of zinc for the aromatization of propane.

The procedure of the preceding examples for the aromatization of propane was followed using catalysts prepared from a ZSM-5 zeolite having a silica/alumina of 520 and containing varying amounts of zinc and 1 wt. % of copper. The conditions and results of these examples are shown in Table IX:

TABLE IX

| Example | 45 | 46 | 47 | 48 | 49 | 50 | 51 | 52 | 53 | 54 | 55 | 56 | 57 |
|---|---|---|---|---|---|---|---|---|---|---|---|---|---|
| Zn (%) | 1.0 | 1.0 | 4.0 | 4.0 | 6.0 | 6.0 | 6.0 | 6.0 | 12.0 | 12.0 | 12.0 | 12.0 | 12.0 |
| Alpha Value | 39.5 | 39.5 | 55.8 | 55.8 | 48.8 | 48.8 | 48.8 | 48.8 | (?) | (?) | (?) | (?) | (?-) |
| Temperature (°F.) | 1000 | 1000 | 986 | 984 | 993 | 988 | 988 | 990 | 1001 | 993 | 993 | 993 | 993 |
| WHSV (g/g hr) | 0.27 | 2.16 | 0.27 | .108 | 1.0 | 4.0 | 2.0 | 1.0 | 1.0 | 2.2 | 1.5 | 0.5 | 1.0 |
| On Stream (hr) | 2.5 | 5.5 | 2.0 | 33.0 | 3.4 | 4.5 | 6.1 | 23.3 | 1.8 | 3.5 | 4.7 | 6.3 | 23.2 |
| Conversion (wt %) | 90.69 | 56.9 | 78.6 | 68.6 | 61.2 | 64.3 | 67.5 | 71.7 | 70.3 | 66.1 | 67.8 | 80.3 | 68.8 |
| Product Yield (%) | | | | | | | | | | | | | |
| Methane | 12.75 | 6.21 | 5.63 | 4.35 | 5.23 | 3.88 | 4.36 | 4.63 | 5.19 | 4.33 | 4.69 | 5.49 | 4.92 |
| Ethylene | 0.46 | 0.67 | 0.63 | 2.16 | 1.26 | 1.56 | 1.45 | 1.34 | 1.33 | 1.41 | 1.35 | 1.05 | 1.35 |
| Ethane | 28.04 | 12.81 | 12.63 | 11.13 | 1.508 | 10.78 | 12.40 | 13.56 | 14.59 | 12.05 | 13.04 | 15.68 | 13.73 |
| Propylene | 0.66 | 0.00 | 1.62 | 0.00 | 0.00 | 0.00 | 0.00 | 0.00 | 0.00 | 0.00 | 0.00 | 2.20 | 0.00 |
| Propane | 9.31 | 43.11 | 21.41 | 31.43 | 28.35 | 35.74 | 32.46 | 28.29 | 29.72 | 33.91 | 32.17 | 19.73 | 31.18 |
| Butenes | 0.00 | 0.46 | 1.21 | 1.14 | 0.97 | 1.73 | 1.40 | 1.05 | 1.02 | 1.46 | 1.26 | 0.49 | 1.11 |
| Butanes | 0.12 | 0.77 | 0.79 | 1.58 | 1.62 | 2.20 | 2.15 | 1.74 | 1.71 | 2.20 | 2.07 | 0.86 | 1.91 |
| $C_5$'s | 0.00 | 0.10 | 0.19 | 0.34 | 0.20 | 0.50 | 0.38 | 0.26 | 0.22 | 0.40 | 0.33 | 0.13 | 0.25 |
| Benzene | 17.04 | 11.01 | 10.06 | 12.89 | 14.25 | 9.63 | 11.56 | 13.32 | 14.51 | 11.71 | 12.77 | 15.37 | 13.25 |
| Toluene | 21.77 | 15.29 | 13.12 | 14.73 | 15.66 | 14.05 | 14.40 | 15.17 | 16.12 | 20.01 | 15.65 | 18.82 | 15.42 |
| Xylenes | 9.08 | 8.21 | 14.92 | 12.59 | 11.70 | 18.83 | 14.16 | 16.25 | 12.64 | 9.66 | 11.33 | 18.62 | 11.75 |
| $C_9$ A | 0.77 | 0.36 | 17.23 | 7.67 | 5.68 | 1.09 | 4.53 | 4.39 | 2.26 | 2.22 | 5.35 | 1.56 | 5.12 |
| Product Selectivity (%) | | | | | | | | | | | | | |
| Aromatics | 53.7 | 61.3 | 70.4 | 69.8 | 66.0 | 67.9 | 66.2 | 68.5 | 64.8 | 66.0 | 66.5 | 67.7 | 66.2 |
| $C_4 + C_5$ | 0.1 | 1.5 | 2.8 | 4.5 | 3.9 | 5.9 | 5.8 | 4.2 | 4.2 | 6.2 | 6.4 | 1.8 | 4.7 |
| $C_1$ + Ethane | 45.0 | 35.2 | 23.2 | 22.6 | 28.4 | 22.8 | 24.8 | 25.4 | 28.1 | 24.8 | 26.1 | 26.4 | 27.1 |
| $C_2=$ | 0.5 | 1.2 | 0.8 | 3.1 | 1.8 | 2.4 | 2.2 | 1.9 | 1.9 | 2.1 | 2.1 | 1.3 | 2.0 |

The results of Table IX show that high conversion rates and aromatics selectivities in the aromatization of propane can be obtained within a wide range of zinc content in the catalyst. However, the optimum zinc content appears to be about 5 wt. % for a ZSM-5 zeolite-based catalyst with a silica/alumina ratio of 520.

I claim:

1. A process for producing aromatic compounds which comprises contacting under conversion conditions, a feed containing at least 50 weight percent of $C_2$ to $C_8$ aliphatic hydrocarbons with a balanced acid/hydrogenation dual function catalyst comprising as the acid component a crystalline zeolite characterized by a Constraint Index within the approximate range of 1 to 12 and an alpha value no higher than about 100 and as the hydrogenation component an added metal constituent comprising at least 50 weight percent of a component consisting of zinc and a metal from Group IB of the Periodic Table, the weight of added metal in said catalyst being between about 0.5 to about 20 percent based on the total weight of catalyst whereby aliphatic hydrocarbons present in said feed are converted to aromatic compounds, and recovering said aromatic compounds, said zeolite as prepared either having a silica/alumina ratio of at least 220, or a silica/alumina ratio below 220 and being either steamed at a temperature of about 700° to 1300° F. for a period of about 0.5 to 20,000 hours or calcined at a temperature of about 800° to 1000° C. for a period of about 1 to 10 hours, to reduce its alpha value to below 100.

2. The process of claim 1 wherein said acid component is a zeolite having an alpha value of about 5 to 60.

3. The process of claim 2 wherein said hydrogenation component consists of about 1 to 10% by weight of zinc plus copper of which about 25 to 95% by weight is zinc.

4. The process of claim 3 wherein zinc is present in an amount of 1 to 4% based on the weight of the catalyst with the alpha value of said zeolite being in the range of 5 to 20 at a 1% by weight zinc content and about 20 to 60 at a 4% by weight zinc content and the limits of the ranges of alpha value at zinc contents between 1 and 4% by weight being in linear relationship with said limits at 1 and 4% by weight zinc content.

5. The process of claim 1 wherein said zeolite as prepared has a silica/alumina ratio below 220 and is steamed at a temperature of about 700° to 1300° F. for a period of about 0.5 to 20,000 hours to reduce its alpha value to below 100.

6. The process of claim 1 wherein said zeolite as prepared has a silica/alumina ratio below 220 and is calcined at a temperature of about 800° to 1000° C. for a period of about 1 to 10 hours to reduce its alpha value to below 100.

7. The process of claim 3 wherein said catalyst is prepared by serially treating said zeolite with a soluble zinc salt, calcining the zeolite, treating the zeolite with a soluble copper salt and again calcining the zeolite to obtain the finished catalyst.

8. The process of claim 1 wherein the conversion conditions include a termperature of from about 800° to about 1200° F., a pressure of from about 0 to about 2000 psig. and a WHSV of from about 0.01 to about 200.

9. The process of claim 1 wherein said crystalline zeolite is selected from the grouping consisting of ZSM-5, ZSM-11, ZSM-12, ZSM-35, and ZSM-38.

10. The process of claim 9 wherein said zeolite is ZSM-5 and said feed is a low value refinery fuel gas.

11. The process of claim 1 wherein said catalyst comprises said zeolite containing said added metal constituent bound with an inorganic oxide matrix material comprising silica.

12. The process of claim 10 wherein said low value refinery fuel gas is selected from the group consisting of light gases from catalytic crackers and reformers, cokers, visbreakers, steam crackers and distillation towers and normally gaseous natural gas condensates.

13. The process of claim 1 wherein said zeolite has a silica/alumina ratio of at least 220.

14. The process of claim 1, wherein the feed comprises at least 50 wt. % ethane.

15. The process of claim 1, wherein the feed comprises at least 50 wt. % propane.

* * * * *